United States Patent
Rubinsztain et al.

(12) 
(10) Patent No.: US 8,399,252 B2
(45) Date of Patent: Mar. 19, 2013

(54) METHODS AND KITS FOR CELL RELEASE

(75) Inventors: Slawomir Rubinsztain, Ballston Spa, NY (US); Prameela Susarla, Clifton Park, NY (US); Reginald Donovan Smith, Schenectady, NY (US); Evelina Roxana Loghin, Rexford, NY (US)

(73) Assignee: General Electric Company, Niskayuna, NY (US)

( * ) Notice: Subject to any disclaimer, the term of this patent is extended or adjusted under 35 U.S.C. 154(b) by 543 days.

(21) Appl. No.: 12/570,032

(22) Filed: Sep. 30, 2009

(65) Prior Publication Data

US 2011/0076764 A1 Mar. 31, 2011

(51) Int. Cl.
*C12N 5/00* (2006.01)

(52) U.S. Cl. ......... 435/378; 435/366; 435/396; 435/402

(58) Field of Classification Search .................. 435/378, 435/396, 402
See application file for complete search history.

(56) References Cited

U.S. PATENT DOCUMENTS

| 7,022,522 B2 | 4/2006 | Guan et al. |
| 2008/0241926 A1 | 10/2008 | Lee et al. |

FOREIGN PATENT DOCUMENTS

| WO | 2006038427 A1 | 4/2006 |
| WO | 2007083344 A1 | 7/2007 |

OTHER PUBLICATIONS

PCT/SE2010/051033 Search Report, Dec. 22, 2010.
PCT/SE2010/051033 Written Opinion, Dec. 22, 2010.
C. Vodouhe et al., "Control of drug accessibility on functional polyelectrolyte multilayer films," Biomaterials, Science Direct, vol. 27, 2006, pp. 4149-4156.
J.F. Liang et al., "Dimethyl sulfoxide induces multilayer aggregates and prolongs survival of primary cultured hepatocytes," Biotechnology Techniques, vol. 11, No. 12, Dec. 1997, pp. 869-872.
J. Azeredo, A.P. Pacheco, I. Lopes, R. Oliveira and M.J. Vieira; "Monitoring cell detachment by surfactants in a parallel plate flow chamber"; Water Science & Technology vol. 47 © IWA Publishing 2003; Abstract 1page.

*Primary Examiner* — Taeyoon Kim
(74) *Attorney, Agent, or Firm* — Michelle L. Cunningham

(57) ABSTRACT

Methods and kits of releasing cells are provided. The method comprises the steps of providing cultured cells on a cell culture support comprising a multi layer polyelectrolyte coating immobilized on a substrate, and releasing the cultured cells from the cell culture support by a releasing solution comprising DMSO. The kit comprises a cell culture support and a releasing solution. The releasing solution comprises DMSO.

12 Claims, 2 Drawing Sheets

METHODS AND KITS FOR CELL RELEASE

FIELD

Figure 1A:
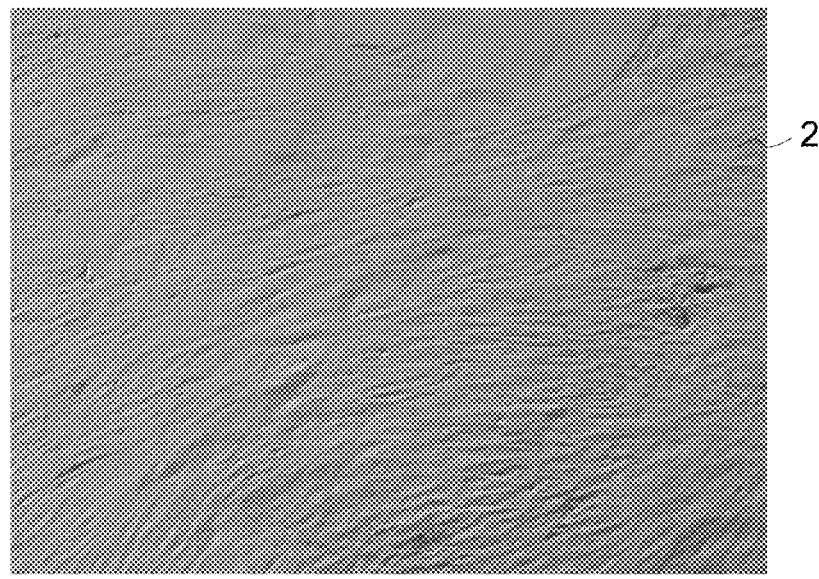

The invention relates to methods for cell release. More particularly, the invention relates to methods for cell release from a polymer-based cell culture support.

BACKGROUND

Adherent cells have conventionally been grown on glass surfaces or on polymer substrates. The surfaces for cell culture are often pre-treated to enhance cell adhesion and proliferation. Matrices for adherent cells that allow on-demand cell detachment or cell release, have long been needed in biomedical and biological applications.

Cultured cells may be detached or released from cell culture supports by a variety of methods. Commonly used cell release methods comprise mechanical methods (such as scraping), treatment with proteolytic enzymes (such as trypsin), use of calcium chelators (such as EDTA), or a combination of such methods. However, many of these conventional cell release methods may cause adverse effects on cultured cells, and may modify their inherent structure and function. For example, treatment of cells with trypsin (i.e., trypsinization) is a harsh method, and is not desirable for delicate cells such as stem cells, due to its potential effect on cell phenotype. Moreover, trypsin is typically derived from animals, and may contain impurities like co-fractionated proteins or biological agents (such as viruses or mycoplasma). Impurities of animal origin may limit the use of released cells for critical applications such as cell therapy. Mechanical methods for releasing cells are labor intensive and are often impractical for industrial-scale cell culture applications.

Other non-enzymatic methods include physical methods that use ultrasounds or shock waves, which generate bubbles that facilitate cell detachment. Cultured cells from cell culture supports comprising thermoresponsive polymers like poly-N-isopropylacrylamide (PNIPAAm) may be released by cooling the cell culture support to a temperature in a range from about 4-20° C.

Efficient cell release is particularly important for high yield in industrial-scale cell culture processes. Therefore, there is an emerging need to develop better cell release techniques for fast, efficient cell detachment without affecting cell morphology and cell viability.

BRIEF DESCRIPTION

The invention generally comprises both methods and kits for releasing cells from a cell culture support.

An example of a method for releasing cells from a cell culture support comprises providing cultured cells on a cell culture support and releasing the cultured cells from the cell culture support by adding a releasing solution. The releasing solution comprises dimethyl sulfoxide (DMSO). The cell culture support comprises a multi-layer polyelectrolyte-based coating on a substrate.

An example of a kit for culturing cells generally comprises a cell culture support, and a releasing solution for cell release. The releasing solution comprises DMSO. The cell culture support comprises a substrate, and a multi-layer polyelectrolyte-based coating on the substrate.

Another example of a method for releasing cells comprises the steps of providing cultured human mesenchymal stem cells on a cell culture support (comprising a multi-layer polyelectrolyte-based coating on a substrate), and releasing the cultured cells from the cell culture support at room temperature by incubating the cells with a releasing solution. The releasing solution comprises about 0.01% DMSO in PBS.

DRAWINGS

Figure 1B:
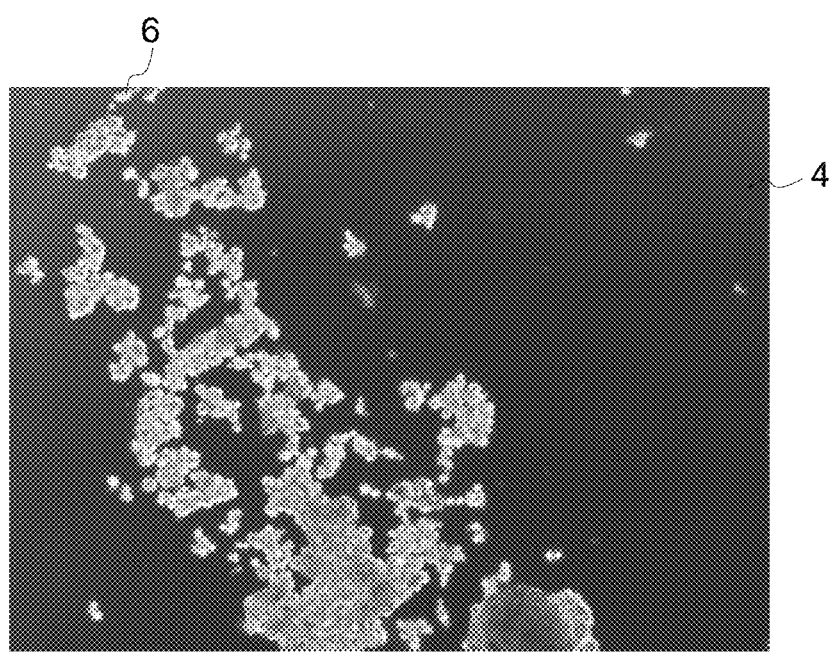

These and other features, aspects, and advantages of the present invention will become better understood when the following detailed description is read with reference to the accompanying drawings in which like characters represent like parts throughout the drawings, wherein:

FIG. 1A is an image of an uncoated glass slide after addition of a releasing solution comprising DMSO. FIG. 1B is an image of a glass slide with a multi-layer polyelectrolyte-based coating after releasing cells using a releasing solution comprising DMSO.

Figure 2:
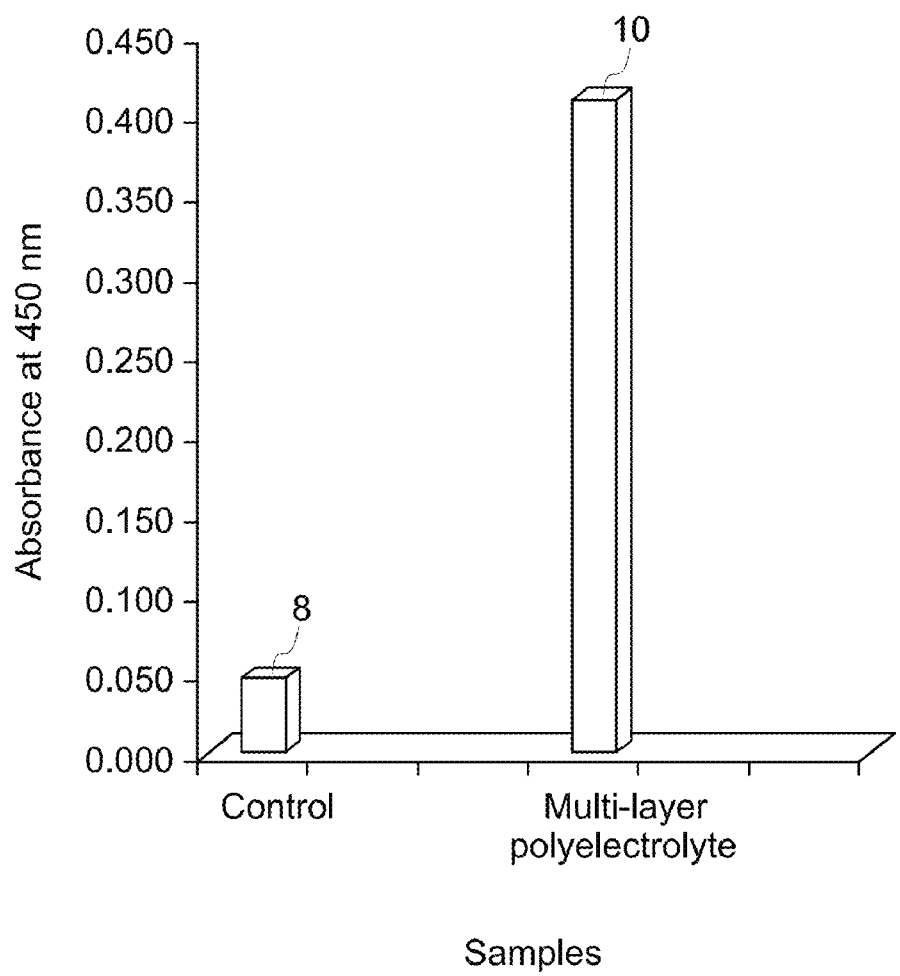

FIG. 2 represents graphical plots of a WST-1 cell assay, illustrating the change in optical density of the WST-1 reagent when mixed with released cells and measured at 450 nm. The optical density at 450 nm correlates with number of cells present in the assay system. Cells were released from uncoated or multi-layer polyelectrolyte coated glass slides using a releasing solution comprising DMSO in PBS.

DETAILED DESCRIPTION

To more clearly and concisely describe the subject matter of the claimed invention, the following definitions are provided for specific terms, which are used in the following description and the appended claims. Throughout the specification, exemplification of specific terms should be considered as non-limiting examples.

A "cell culture support", as referred to herein, is a support for adhering and culturing cells. The cell culture support may comprise a substrate. The substrate may be coated or layered with a suitable coating material for cell adherence and proliferation. Suitable coating materials may include, but are not limited to, polyelectrolytes.

A "substrate", as referred to herein, is a base or a holder, which provides support for a coating. The coated substrate may be used as a cell culture support.

A "releasing solution", as referred to herein, is a solution that helps to release or detach cells from a cell culture support. The releasing solution comprises one or more polar aprotic solvents, e.g. dimethyl sulfoxide (DMSO). For example, DMSO belongs to a family of polar aprotic solvents, which are water miscible. Other polar aprotic solvents include but are not limited to: tetrahydrofurane, acetone, N,N-dimethylformamide. Those solvents strongly interact with polymers such as polyelectrolytes and are capable to disturb hydrogen bonds as well as electrostatic interactions, which affect polymer aggregation and cell adhesion. The releasing solution comprises DMSO in phosphate buffered saline (PBS).

"Polyelectrolytes" as referred to herein, are polymers wherein the repeating units of the polymer bear an electrolyte group. The polymers become charged while these groups are dissociated in aqueous solutions (e.g., water). Polyelectrolyte properties are thus similar to both electrolytes (salts) and polymers (high molecular weight compounds), and are sometimes called polysalts. The polyelectrolyte solutions are electrically conductive like salts and are often viscous like polymers. Many biological molecules are polyelectrolytes. Examples of polyelectrolytes include but not limited to polypeptides (or proteins), DNA, and polymers.

A high yield of healthy, viable cells is required for applications such as drug screening and cell therapy. Industrial-scale cell manufacturing units or cell bioreactors often employ suitable cell culture supports for culturing cells. Efficient non-enzymatic methods for releasing cells from the cell culture support can be particularly useful if the cultured cells are to be used in therapeutic applications.

The methods and kits of the invention for releasing cells from a cell culture support are useful for delicate cells, such as stem cells. Efficient release of normal cells or delicate cells may acquire using the methods and kits for cell release of the present invention.

One example of the method for releasing cultured cells comprises the steps of: providing cultured cells on a cell culture support, and releasing the cultured cells from the cell culture support by adding a releasing solution comprising DMSO. The cell culture support may comprise multiple layers (multi-layer) of polyelectrolyte immobilized on a substrate.

The cells are released using a releasing solution comprising DMSO. The concentration of DMSO (v/v) in the releasing solution may range from about 0.01% to 1.0%. In some embodiments, the concentration of DMSO in the releasing solution may range from about 0.02% to 0.5%, and 0.1% to 0.5%. Cell release efficiency may be enhanced by changing the concentration of DMSO in the releasing solution. The efficiency for cell release may increase with increasing concentrations of DMSO. The releasing solution may further comprise DMSO in a phosphate buffered saline (PBS) wherein pH of the solution is about 7.5.

The release of the cultured cells may be further optimized by incubating the cell culture support with the releasing solution at room temperature or in ranges from about 15° C. to 37° C., about 20° C. to 35° C. or about 20° C. to 30° C.

The cells may be released from the cell culture support by incubating on the cell culture support at room temperature for various periods of time, such as, for about 1 hr to 2 hrs, about 30 min to 1 hr, or about 10 min to 30 min. In some embodiments, cell release efficiency may be modified, by changing incubation time for cell release after adding releasing solution. For example, cell release efficiency may be increased with increasing incubation time.

The method for releasing cells comprises the step of providing cultured cells on a cell culture support. The method may include culturing the cells on the cell culture support. The cells may be cultured at a various temperature ranges from about 20° C. to 37° C., about 30° C. to 37° C. and about 35° C. to 37.5° C., depending on, for example, cell type.

The cells may be grown in a culture flask and may be added to the cell culture support for further growth. Cells may be grown on the cell culture support after extraction from a biological source such as, but not limited to, blood, bone marrow, or tissue section. In some other embodiments, the cell culture support may be introduced in a spinner flask, a stacked culture flask, a stirred tank reactor, or any other in-vitro cell culture system.

The methods may also be used to release fragile cells once they are cultured on the cell culture support. The fragile cells may include, but are not limited to, embryonic stem cells, adult stem cells, induced pluripotent stem cells, dendritic cells, hematopoietic cells, mesenchymal stromal cells, neural cells, reprogrammed cells, or de-differentiated cells. For example, cultured stem cells are released from the cell culture support by incubating the cell culture support with a releasing solution comprising 0.01% (v/v) of DMSO for a period of about 10 min.

Efficient methods for stem cell culture are critical to generate stem cells having high purity in good yield for use in clinical or research applications. Culture of stem cells often require specialized techniques since the stem cells may lose their multipotency or pluripotency or may differentiate during cell culture. More over, conventional methods of releasing cells, such as mechanical scraping or trypsinization, may not be suitable for releasing the cultured stem cells. These issues may be addressed by using one of the non-enzymatic examples of the methods for releasing cells. For example, mesenchymal stromal cells may be successfully cultured and released using the non-enzymatic, DMSO-based cell release method described herein without any detrimental effects on the cultured mesenchymal stromal cells.

The cell culture support may be configured as a cell culture bed, a cell carrier bead, disk or scaffold comprising one or more polymeric layers. Non-limiting examples of substrates include a microcarrier, a membrane, a fiber, a hollow fiber, a capillary, a vessel, a flask, a disc, a bead, a Petri dish, a plate, a woven or non-woven fabric or mesh, a nano-fiber mat, a particle, a scaffold or a foam. Examples of substrate materials include, but are not limited to, glass, polymer, metal, ceramic and combinations thereof.

The cell culture support may comprise a multi-layer polyelectrolyte-based coating. The multi-layer polyelectrolyte-based coating may comprise at least one copolymer layer or at least one homopolymer layer. In other embodiments, the multi-layer polyelectrolyte-based coating may comprise at least one copolymer layer and at least one homopolymer layer. The copolymer layers and the homopolymer layers may also be stacked in the coating in an alternating arrangement. For example, the cell culture support may comprise alternate blocks of a copolymer layer and/or a homopolymer layer. The multiple layers of polyelectrolyte-based coating may be fabricated by utilizing a layer-by-layer (LBL) technique. One or more polymer layers may be arranged one over another by using the LBL technique.

The multi-layer polyelectrolyte-based coating may comprise a copolymer wherein the copolymer may be a block copolymer. The coating may comprise multiple layers of identical or different block copolymers. A non-limiting example of a block copolymer is a thermoresponsive amphiphilic block copolymer (TRABC). The block copolymer may comprise poly(di(ethylene glycol) methylether methacrylate)-co-poly(acrylic acid). In addition to the block copolymer, the multi-layer coating may further comprise one or more additional polymer layers (e.g. homopolymer or copolymer). Non-limiting examples of homopolymers include poly (L-lysine), poly(allylamine), poly(ethylene imine) and poly(vinylpyrrolidone).

The homopolymer or copolymer in the multi-layer polyelectrolyte coating may be responsive to one or more external stimuli such as temperature, pH, or ionic strength. The homopolymer may be responsive to ionic strength or pH or both. The copolymer may be responsive to temperature or pH or both.

The multi-layer polyelectrolyte-based coating may be adhered to a substrate via non-covalent interaction. Attaching the polymer coating non-covalently to the substrate offers significant advantages, such as, the flexibility to use the substrate in complex substrate geometries (e.g., flat sheets, beads, cubes, porous foams, fibers and nonwovens).

An embodiment of the kit of the invention, for culturing and releasing cells, may comprise a cell culture support having a substrate with multi-layer polymer-based coating on the substrate, and a releasing solution. The kit may further comprise cells (e.g., in a frozen condition) and/or medium for culturing cells. The kit may further comprise a protocol for handling, culturing and/or releasing cells from the cell culture support. The kit may be packaged along with a manual describing the method of using the kit.

EXAMPLE 1

Preparation of Multi-Layer Polymer Coated Cell Culture Support

Multi-layer polymer coated cell culture supports were prepared as follows. Poly-L-Lysine (PLL) coated glass slides (Polysciences Inc.) were diced into 8×8 mm squares. The slides were washed with de-ionized (DI) water and with absolute ethanol followed by air-drying at room temperature. The dry slides were immersed into 0.1% solution of poly(di(ethyleneglycol)methylether methacrylate)-co-poly(acrylic acid) (PDEGMEMA-co-PAA) in DI water at 37° C. for 60 minutes. The slides were then washed with DI water and were incubated with 0.1% solution (w/v) of Poly-L-Lysine (Aldrich) for 60 minutes at 37° C. The 0.1% solution of poly-L-Lysine (PLL) contained a small amount (about 0.1 mol %) of poly-L-lysine functionalized with fluorescein 5-isothiocyanate (FITC-PLL) (FITC from Sigma) fluorescent probe. Introduction of a fluorescent probe enables the measurement of the fluorescence intensity of polymer layers to determine proper formation of multi-layer coatings. The slides were washed with warm (37° C.) DI water and were then incubated with 0.1% solution (w/v) of poly(di(ethyleneglycol)methylether methacrylate)-co-poly(acrylic acid) for 60 min at 37° C. Slides were washed with DI water and air-dried. The amount of deposited PLL was determined by measuring the intensity of FITC florescence on a Typhoon fluorescence imager.

Quantitative analysis of the measured fluorescence confirmed the formation of PLL/PDEGMEMA-co-PAA five-layer coating (FITC bound). The formation of PLL/PDEGMEMA-co-PAA coating on the substrate was additionally confirmed by time of flight secondary ion mass spectrometry (ToF SIMS) analysis (data not shown). The ToF SIMS spectra showed a gradual decrease in the peak height and peak position for the observed negative $SiO_2$ ions. The LBL coating of samples having five PLL/PDEGMEMA-co-PAA layers was thick enough that $SiO_2$ ions were almost undetectable (data not shown) with respect to an uncoated glass slide.

EXAMPLE 2

Cell Culture on the Multi-Layer Cell Culture Support and Subsequent Cell Release The cell culture support was used to culture human mesenchymal stem cells (hMSC, ATCC). These cells were first cultured on polystyrene surfaces using the Mesenchymal Stem Cell Growth Medium (PT-3001, Lonza). To culture cells, about $10^5$ human mesenchymal stem cells (primary culture) were seeded on the surface of the cell culture support (uncoated and/or coated glass slides) and incubated at 37° C., in a humidified atmosphere of 5% $CO_2$.

Cells were allowed to proliferate for one week on uncoated and/or on polymer-coated glass surfaces in the cell culture incubator. Cell expansion was monitored by bright field microscopy and medium was exchanged every 3-4 days. Cell-release was tested by adding a releasing solution comprising 0.01% (v/v) DMSO in PBS. Media was removed from the cell culture support (uncoated or coated glass slides) when the cells were ~100% confluent. The cells were rinsed with PBS followed by addition of enough releasing solution to cover the growth surface with attached cells. The cell culture support with releasing solution was incubated for 30 minutes at a room temperature. The cells were observed in an inverted microscope until the cell layer was dispersed. Subsequently, released cells were removed from the cell culture support by pipetting out from the cell culture support. FIG. 1A shows an image of an uncoated cell culture support (2) after the attempt of releasing cultured human mesenchymal stem cells by using a releasing solution comprising 0.01% (v/v) DMSO. FIG. 1B shows an image of multi layer PLL/PDEGMEMA-co-PAA (five layers) coated cell culture support (4) after the release of human mesenchymal stem cells (6) by using a releasing solution comprising 0.01% (v/v) DMSO.

EXAMPLE 3

Quantitative Estimation of Released Cells

The quantitative measurement of cell release is presented in FIG. 2 by measuring the optical density of the cell proliferation assay solution at 450 nm using WST-1 assay reagent. Released cells were pelleted down by centrifuging the cell suspension at 500 g for 5 min. The pelleted cells were resuspended in 200 μl growth medium and were transferred in 96 well plate. The plate was spun down at 500 g for 5 min. 150 μl fresh growth medium and 15 μl of WST-1 cell assay reagent were added to each well. Cells with assay reagent were incubated at 37° C. for 2.5 hr. This experiment was performed in replicates of 3 different sets. Cell release from uncoated glass slides (bar 8), and five layers of PLL/PDEGMEMA-co-PAA coated glass slides (bar 10) are shown in FIG. 2. The data shows efficient cell release for the five layers of PLL/PDEGMEMA-co-PAA coated glass slides (10) compared to uncoated surface of the glass slide (8). An uncoated glass slide served as a control. The difference between the signal for released cells from uncoated glass slide and signal for released cells from five layer PLL/PDEGMEMA-co-PAA coated glass slide gives a measure of the release efficiency, which as indicated by FIG. 2 is clearly efficient for multi-layer polymer coated cell culture support.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A method of releasing cells, comprising:
   a) providing cultured cells on a cell culture support, wherein the cell culture support comprises a multi-layer polyelectrolyte coating immobilized on a substrate, wherein the multi layer polyelectrolyte coating comprises at least one layer of poly-(di(ethyleneglycol)methylether methacrylate)-co-polyacrylic acid and
   b) releasing the cultured cells from the cell culture support by adding a releasing solution comprising DMSO, wherein the cells are selected from the group consisting of embryonic stem cells, adult stem cells, induced pluripotent stem cells, dendritic cells, hematopoietic cells, mesenchymal stromal cells, neural cells, reprogrammed cells and de-differentiated cells.

2. The method of claim 1, wherein the cultured fragile cells comprise mesenchymal stromal cells.

3. The method of claim 1, wherein the cultured fragile cells comprise human mesenchymal stromal cells.

4. The method of claim 1, wherein concentration of DMSO in the releasing solution ranges from about 0.01% to 1.0%.

5. The method of claim 1, wherein concentration of DMSO in the releasing solution ranges from about 0.02% to 0.5%.

6. The method of claim 1, wherein concentration of DMSO in the releasing solution ranges from about 0.1% to 0.5%.

7. The method of claim 1, wherein the cultured cells are released from the cell culture support by incubating the cell culture support at room temperature.

8. The method of claim 7, wherein the incubation is performed for about 10 to 30 minutes.

9. The method of claim 1, wherein the multi layer polyelectrolyte coating comprises at least one homopolymer layer.

10. The method of claim 1, wherein the multi layer polymer coating comprises an alternating arrangement of a poly-(di(ethyleneglycol)methylether methacrylate)-co-polyacrylic acid layer and a homopolymer layer.

11. The method of releasing cells of claim 1, wherein the multi layer polyelectrolyte coating comprises at least one layer of poly-L-lysine.

12. A method of releasing human mesenchymal stem cells, comprising:
   a) providing cultured human mesenchymal stem cells on a cell culture support, wherein the cell culture support comprises a multi-layer polyelectrolyte coating immobilized on a substrate, wherein the multi-layer polyelectrolyte coating comprises at least one poly-(di(ethyleneglycol)methylether methacrylate)-co-polyacrylic acid layer; and
   b) releasing the cells from the cell culture support at room temperature, by incubating with a releasing solution comprising about 0.1% DMSO.

* * * * *